United States Patent [19]

Ward

[11] Patent Number: 4,978,386
[45] Date of Patent: Dec. 18, 1990

[54] HERBICIDAL 2-(SUBSTITUTED-PHENYL)-3-AMINO-2-CYCLOPENTENONE DERIVATIVES

[75] Inventor: Carl E. Ward, San Jose, Calif.

[73] Assignee: Chevron Research Company, San Francisco, Calif.

[21] Appl. No.: 794,345

[22] Filed: Oct. 31, 1985

Related U.S. Application Data

[63] Continuation-in-part of Ser. No. 743,466, Jun. 11, 1985, abandoned.

[51] Int. Cl.$^5$ .................... A01N 33/02; A01N 43/00; A01N 43/02; A01N 43/40; C07D 333/22; C07C 211/00

[52] U.S. Cl. ......................................... 71/121; 71/88; 71/90; 71/94; 71/95; 71/98; 71/105; 71/106; 549/77; 549/496; 564/307; 564/308; 564/428; 564/440; 564/442; 546/283; 546/284; 546/330; 546/339; 548/517; 548/527; 548/571; 558/414

[58] Field of Search ................... 71/88, 90, 94, 95, 98, 71/105, 106, 121; 549/77, 496; 564/307, 308, 428, 440, 442; 546/283, 284, 330, 339; 548/517, 527, 571; 558/414

[56] References Cited

U.S. PATENT DOCUMENTS

| | | | |
|---|---|---|---|
| 3,097,136 | 7/1963 | Godefroi | 167/65 |
| 3,577,433 | 5/1971 | Fulks et al. | 260/3265 |
| 4,209,532 | 6/1980 | Wheeler | 424/331 |
| 4,256,658 | 3/1981 | Wheeler | 260/465 D |
| 4,283,348 | 8/1981 | Wheeler | 240/465 D |
| 4,419,724 | 12/1983 | Swithenbank | 71/127 |
| 4,441,910 | 4/1984 | Shapiro | 71/90 |
| 4,464,536 | 8/1984 | Scherer | 546/213 |
| 4,537,623 | 8/1985 | Ward | 71/90 |
| 4,568,376 | 2/1986 | Ward | 71/88 |
| 4,568,377 | 2/1986 | Ward | 71/88 |
| 4,568,378 | 2/1986 | Ward | 71/88 |
| 4,596,595 | 6/1986 | Ward | 71/90 |
| 4,606,756 | 8/1986 | Ward | 71/94 |

FOREIGN PATENT DOCUMENTS

| | | | |
|---|---|---|---|
| 3429437 | 6/1985 | Fed. Rep. of Germany | 549/77 |
| 42-19090 | 9/1967 | Japan . | |
| 44-52222 | 3/1969 | Japan . | |
| 44-13710 | 6/1969 | Japan . | |
| 0062248 | 4/1982 | Japan | 549/496 |
| 1521092 | 8/1978 | United Kingdom . | |

OTHER PUBLICATIONS

Journal of Organic Chemistry, vol. 49, p. 228 (1984).
Letrahedron Letters, No. 40, p. 4125 (1976).
Chemical-Zeitung, vol. 104, No. 10, p. 302 (1980).
J. Chem. Soc. Trans. I, p. 1539 (1984).
Helvetica Chemica Acta, vol. 66, pp. 362-378 (1983).

Primary Examiner—Alan Siegel
Attorney, Agent, or Firm—R. C. Gaffney; L. S. Squires

[57] ABSTRACT 2-(3-substituted phenyl)-3-amino-2-cyclopentenone derivatives. The compounds generally exhibit both pre-emergence and post-emergence phytotoxicity and are useful as herbicides and also at low dosages as plant growth regulating agents.

52 Claims, No Drawings

HERBICIDAL 2-(SUBSTITUTED-PHENYL)-3-AMINO-2-CYCLOPENTENONE DERIVATIVES

CROSS REFERENCE TO RELATED APPLICATIONS

This application is a continuation-in-part of U.S. application Ser. No. 743,466, filed June 11, 1985 and now abandoned.

BACKGROUND OF THE INVENTION

This invention relates to 3-amino-2-(substituted-phenyl)-2-cyclopentenone derivatives and to the use of such compounds as herbicides and plant growth regulators.

An academic paper appears in the Journal of Organic Chemistry vol. 49, pp. 228–236 (1984) describing the preparation of 3-amino-2-[3,4(methylenedioxy)phenyl]-cyclopentenone in studies relating to the synthesis of Harringtonine alkaloids. The preparation of 4-amino-3-(a, a, a-trifluoro-m-tolyl)-spiro[4,5]deca-3,6,9-triene-2,8dione; i.e.,

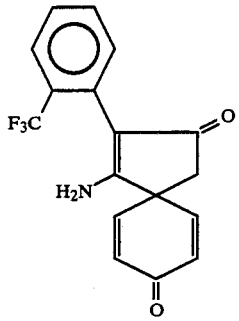

is described in an academic paper appearing in *Tetrahedron Letters* No. 40, pp. 4125–4128 (1976).

*Chemiker-Zeitung* 104 (1980) No. 10, Pages 302–303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application No. 13,710/69 (Chemical Abstracts 71:61195e) discloses the generic formula for 5-amino-3-oxo-4-(phenyl and halophenyl)-2,3-dihydrofuran and specifically discloses 5-amino-3-oxo-4-(phenyl and 4-chlorophenyl)-2,3-dihydrofurans. Japanese Patent No. 19090 (Chemical Abstracts 69P10352e) discloses certain 2,3-dihydrothiophenes as pharmaceuticals. *Helvetica Chemica Acta*, Volume 66, Pages 362–378 (1983) discloses 5-N-cyclopropyl-4-phenyl-2-methoxycarbonylmethylene-3-furanone as part of an academic chemical synthesis discussion. U.S. Pat. No. 4,441,910 discloses herbicidal ureidosulfonylfurans and ureidosulfonylthiophenes.

My copending U.S. application Ser. Nos. 607,610, filed May 9, 1984, and now abandoned; 723,768, filed Apr. 16, 1985, and now U.S. Pat. No. 4,568,376; 666,075, filed Oct. 26, 1984, now U.S. Pat. No. 4,568,375; 594,497, filed Mar. 29, 1984, now U.S. Pat. No. 4,537,623; 684,977, filed Dec. 21, 1984, now U.S. Pat. No. 4,658,378 and 727,459, filed Apr. 26, 1985, now U.S. Pat. No. 4,568,377, disclose and claim certain 2-substituted-5-amino and substituted amino-3-oxo-4-substituted phenyl-2,3-dihydrofuran derivatives having herbicidal activity. My copending U.S. application Ser. No. 623,805, filed June 22, 1984, now U.S. Pat. No. 4,596,595, discloses and claims certain 2-substituted-5-amino and substituted amino-3-oxo-4-substituted phenyl-2,3-dihydrothiophene herbicides.

SUMMARY OF THE INVENTION

The present invention provides compounds having both pre-emergence and post-emergence herbicidal activity and having especially good pre-emergence activity against a broad spectrum of both broad-leaf weeds and grassy weeds. The present compounds exhibit exceptional pre-emergence activity against grassy weeds. Further by proper dosage regulation certain of the compounds can be safely and effectively used as pre-emergent herbicides against both grasses and broad-leaf weeds in a number of important broadleaf crops including soybean, cotton and peanuts. At lower application rates certain of the compounds also exhibit plant growth regulating properties.

The compounds of the present invention can be represented by the following formula:

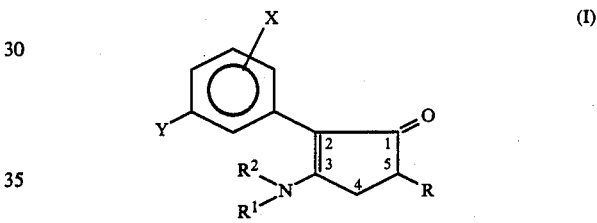

wherein R is lower alkyl having 1 through 4 carbon atoms; cycloalkyl having 3 through 7 carbon atoms, lower alkenyl; fluoroalkyl having 1 through 4 carbon atoms and 1 through 3 fluorine atoms; haloalkenyl having 2 through 4 carbon atoms and 1 through 3 halo atoms independently selected from the group of fluoro, chloro, bromo, or iodo; lower alkoxyalkyl wherein the alkoxy and alkyl moiety thereof independently have 1 through 3 carbon atoms; lower alkylthioalkyl wherein the alkyl moieties independently have 1 through 3 carbon atoms; phenyl; naphth-1-yl; inden-1-yl; 4-fluorophenyl; 4-chlorophenyl; thienyl; furyl; arylalkylene having 1 through 3 carbon atoms in the alkylene moiety and wherein said aryl moiety is phenyl, naphth-1-yl or inden-1-yl; or substituted aryl or arylalkylene selected from the group having the formulas:

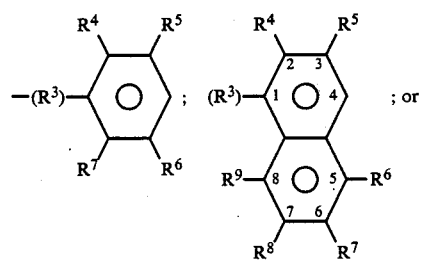

-continued

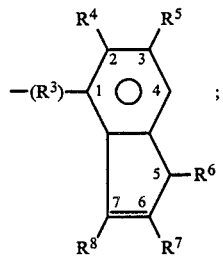

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen; and $R^3$ is a single bond or an alkylene having 1 through 3 carbon atoms;

$R^1$ is hydrogen or alkyl having 1 through 4 carbon atoms;

$R^2$ is hydrogen, alkyl having 1 through 4 carbon atoms, alkenyl having 3 or 4 carbon atoms, alkoxycarbonylalkyl having from 1 through 4 carbon atoms in the alkoxy moiety and from 1 through 4 carbon atoms in the alkyl moiety alkoxyalkyl wherein the alkoxy and alkyl moieties independently have 1 through 3 carbon atoms or alkylthicalkyl wherein the alkyl moieties independently have 1 through 3 carbon atoms; or $R^1$ and $R^2$ together with the nitrogen to which they are joined form a saturated or unsaturated nitrogen heterocycle having 5 or 6 ring atoms one of which is nitrogen and the remainder of which are carbon atoms;

X is hydrogen, lower alkyl, lower alkoxy, halo, or trifluoromethyl and can be at any available position on the phenyl ring; and Y is lower alkyl, lower alkoxy; halo; cyano; nitro; lower haloalkyl having 1 through 4 carbon atoms and 1 to 3 of the same or different halo atoms; lower haloalkoxy having 1 through 4 carbon atoms and 1 through 3 of the same or different halo atoms; or lower haloalkylthio having 1 through 4 carbon atoms and 1 through 3 of the same or different halo atoms.

The invention also comprises compatible salts of the compound of Formula (I), for example, acid addition salts with respect to the exocyclic amino group; and also salts obtained via replacement of the amino hydrogen (i.e., $R^1$ and $R^2$ is hydrogen) with a compatible cation or enolation of the 1-oxo group following replacement of the amino hydrogen.

The compounds of Formula (I) exist as keton⇌enol isomers. The compounds also have an asymmetric carbon atom and can also exist as optical isomers In some instances the compounds also exist as geometric isomers. The above formula is intended to encompass the respective individual isomers as well as mixtures thereof and the respective isomers as well as mixtures thereof are encompassed within the invention.

It has also been discovered that the presence of a 3-trifluoromethyl substituent on the 4-phenyl group of the compounds of the present invention generally very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 2–7 set forth hereinbelow on Pages 21–40. In terms of substituents, the preferred compounds are those wherein R is lower alkyl, thienyl, furyl, aryl or substituted aryl, more preferably methyl, ethyl, propyl, phenyl or substituted phenyl, and especially phenyl, monomethylphenyl or monohalophenyl, more especially methyl, ethyl, propyl, phenyl, 2-thienyl, 3-thienyl, 2halophenyl, 2-lower alkylphenyl, or 4-fluorophenyl; $R^1$ and $R^2$ are independently hydrogen, methyl, ethyl or n-propyl, and more preferably one of $R^1$ or $R^2$ is hydrogen and the other is methyl, ethyl or n-propyl, more preferably methyl or ethyl, especially ethyl; X is hydrogen and/or Y is trifluoromethyl or halo, especially 3-trifluoromethyl. Most preferably the compounds contain a combination of two or more preferred substituents.

The compounds of Formula (I) wherein $R^1$ and $R^2$ are each hydrogen can be conveniently prepared by the following schematically represented process:

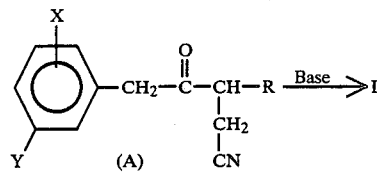

wherein R, X and Y are as defined hereinabove.

This process can be conveniently effected by contacting Compound (A) with a strong base, preferably in an inert organic solvent.

Typically, this process is conducted at temperatures in the range of about from 0° to 100° C., preferably 60° to 80° C., for about from 1 to 24 hours, preferably 12 to 18 hours, using about from 1.0 to 2.0, preferably 1.0 to 1.5 moles of base per mole of Compound (A).

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

The compounds of Formula (I), wherein R is hydrogen and $R^1$ and $R^2$ are hydrogen can also be conveniently prepared by treating the corresponding 3-chloro or 3-bromo analog with ammonia

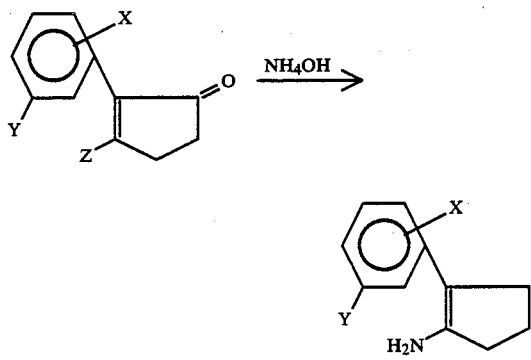

wherein Z is chloro or bromo and X and Y are as defined hereinabove.

This process is typically conducted by contacting the 3-chloro or 3-bromo analog with a stoicheometric excess of ammonium hydroxide at temperatures in the range of about 0° to 30° C. for about from 1 to 72 hours. Preferably, the reaction is conducted in an inert organic solvent, such as, for example, tetrahydrofuran, dioxane, dimethoxyethane, diethyl ether and the like, and compatible mixtures thereof. The 3-chloro or 3-bromo analogs can be prepared by treatment of the corresponding 3-hydroxy analog with sodium hydride to afford the sodium salt followed by treatment with oxalyl chloride (bromide) in refluxing benzene (as described in J. Org. Chem. 49,228 (1984)).

The starting materials of Formula (A) can be prepared by the following schematically represented process:

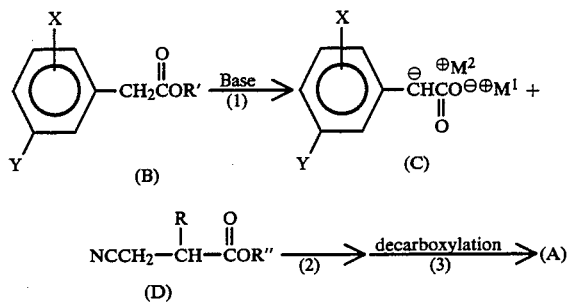

wherein R' is hydrogen or lower alkyl, preferably hydrogen; R" is lower alkyl, preferably, methyl or ethyl; $M^1$ and $M^2$ are the same or different cations; and R, X and Y are as defined hereinabove.

Although this process is schematically shown as three steps, the steps are typically and conveniently conducted in situ. Also as is conventional with such reactions the reactions are preferably conducted under substantially anhydrous conditions under an inert gas (e.g., nitrogen).

The first step of this process can be effected by contacting Compound (B) with a non-nucleophilic strong base, preferably in an inert organic solvent. This step is typically conducted at temperatures in the range of about from −78° to 25° C. for about from 0.5 to 5.0 hours using about from 2 to 4, preferably 2 to 2.6, mole equivalents of non-nucleophilic base per mole of Compound (B'). Suitable non-nucleophilic strong bases which can be used include, for example, alkali metal amides, e.g., lithium bis(trimethylsilyl)amide; sodium bis(trimethylsilyl)amide; potassium bis(trimethylsilyl)amide; lithium diethylamide, lithium diisopropyl amide; sodium dimethylamide, and the like. The alkali metal amides are generally known compounds and can be prepared by known procedures, or obvious modifications thereof For example, the alkali metal amides can be prepared by the reaction of a secondary amine with an alkyl alkali metal.

Suitable inert organic solvents, which can be used, include, for example, tetrahydrofuran, dioxane, dimethoxyethane, diethyl ether, diisopropyl ether, and the like and compatible mixtures thereof.

Because replacement of R' proton does not require as strong of base as does replacement of the methylene hydrogen proton, this step can also be conducted in two steps by first using a less strong non-nucleophilic base, and generally less expensive base such as for example alkali metal hydrides, e.g., sodium hydride, to replace the acid proton (R'). The methylene hydrogen can then be replaced as described above but, using only about one-half the amount of alkali metal amide. The two replacements are conveniently conducted in situ.

The second step can be effected by contacting Compound (C) with Compound (D) preferably in an inert organic solvent. As before noted, this process step is preferably conducted in situ with the reaction product mixture of the first step. Typically the second step is conducted at temperature ranges of about from −30° to 25° C. for about from 1 to 24 hours using about from 1.0 to 2.0, preferably 1.0 to 1.1 mole equivalents of Compound (D) per mole of Compound (C). Suitable solvents which can be used include those listed above with respect to the first step and the like.

The decarboxylation (step 3) occurs almost spontaneously and generally can be effected by merely contacting the reaction product of the second step with water, or a weakly acid solution, at temperatures in the range of 0° to 25° C. Conveniently ambient temperatures are used.

The starting materials of Formulas (B) and (D) are generally known materials and can be prepared by known procedures, or obvious modifications thereof (i.e., substitution of appropriate starting materials). The preparation of Compound (B) is for example described in Org. Syn. Coll. Volume 1, 436 (1941), and the preparation of Compound (D) is described in Tetrahedron 39, 3055 (1983).

The compounds of Formula (D) can be, for example, prepared via the following schematically represented procedure

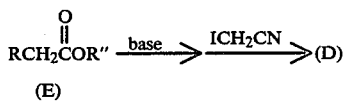

wherein R and R" are as defined hereinabove

This process can be effected by contacting Compound (E) with a strong base to yield the salt and then contacting the salt with iodoacetonitrile. Typically, the two reactions are conducted in situ, in an inert organic solvent.

Typically, the two steps are conducted at temperatures in the range of about from −78° to 25° C., preferably −78° to 0° C., for about from 4 to 24 hours using about from 1.0 to 2.0, preferably 1.0 to 1.1, mole equivalents of base and 1.0 to 2.0, preferably 1.0 to 1.1 moles of iodoacetonitrile per mole of Compound (E).

Suitable non-nucleophilic bases which can be used include, for example, alkali metal hydrides, e.g., sodium hydride, potassium hydride, etc.; alkali metal amides, e.g., lithium bis(trimethylsilyl)amide; sodium bis(trimethylsilyl)amide; potassium bis(trimethylsilyl)amide; lithium diethylamide, lithium diisopropyl amide; sodium dimethylamide, and the like. Suitable inert organic solvents, which can be used, include, for example, tetrahydrofuran, dioxane, dimethoxyethane, diethyl ether, diisopropyl ether, and the like and compatible mixtures thereof.

The compounds of Formula (E) are generally known compounds and can be prepared via known procedures or obvious modifications thereof. Iodoacetonitrile is a known compound.

The compound of Formula (I) wherein one or both of $R^1$ and $R^2$ are substituted can be prepared by alkylation of the amino group of the corresponding compounds for formula I":

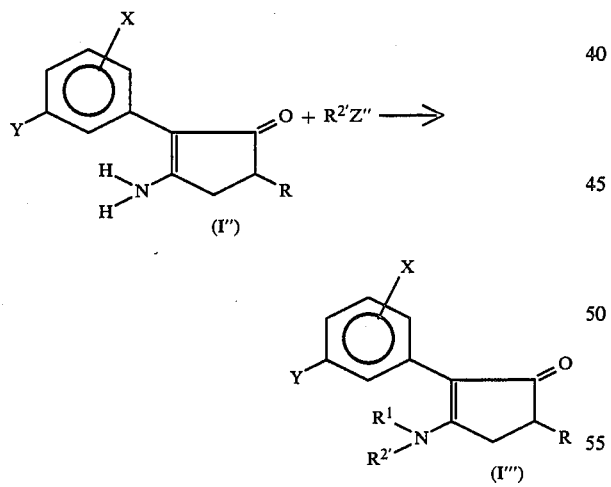

wherein R, $R^1$, X and Y are as defined hereinabove; and $R^{2'}$ is as defined for $R^2$ but is not hydrogen; and $R^{2'}Z''$ is an alkylation agent having the appropriate $R^{2'}$ or appropriate $R^1$ group if dialkylation is desired.

This process can be effected by contacting Compound (I") with a suitable alkylation agent capable of alkylating primary or secondary amino groups.

For example, this can be effected by contacting Compound (I") with $R^{2'}$ iodide or bromide, preferably in an inert organic solvent and preferably in the presence of a scavenger base. Typically, this process is conducted at temperatures in the range of about from 0° to 100° C., preferably 20° to 45° C. for about from 1.0 to 72.0, preferably 2.0 to 18.0 hours. Where it is desired to monoalkylate, then typically about from 1.0 to 1.1 moles of $R^{2'}$ halide reactant is used per mole of Compound (I"). Where it is desired to alkylate both amino hydrogens, then typically about from 1.9 to 4.0 moles of $R^{2'}$ halide are used per mole of Compound (I"). In the case where it is desired to prepare the compound wherein $R^{2'}$ is alkoxyalkyl or alkylthioalkyl, it is preferred to use a large excess of $R^{2'}$ halide even where monoalkylation is desired; for example 3 to 6 moles of $R^{2'}Z''$ per mole of I". Further alkylation can be effected in a second step if desired Also variation in $R^1$ and $R^2$ can be effected by first alkylating only one of the two amino hydrogens and then alkylating the second amino hydrogen with an alkylating agent having a different $R^{2'}$ group. The compounds wherein $R^1$ and $R^2$ together with the amino nitrogen atoms form a saturated heterocycle can be prepared by using the appropriate $Z''-(CH_2)_{2-5}-Z''$, wherein $Z''$ is Cl or Br alkylating agent. The $R^1R^2N$ unsaturated heterocycle can be prepared by using the appropriate cis-alkenyl dihalide, wherein one of the halo atoms is on each of the terminal alkenyl carbon. Suitable inert organic solvents which can be used, include, for example, liquid halogenated alkanes; for example, methylene chloride, carbon tetrachloride, or dichloroethane; also useful are tetrahydrofuran and the like. Suitable scavenger bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

The compounds of Formula (I''') wherein $R^1$ is lower alkyl (e.g. methyl) and $R^2$ is hydrogen or lower alkyl, are advantageously prepared using dialkyl sulfate as the alkylating agent. This can be conveniently effected by contacting the compound of Formula I wherein one or both of $R^1$ and/or $R^2$ are hydrogen with the desired lower alkyl sulfate in the presence of a strong base and preferably in an inert organic solvent in the presence of a phase transfer agent. Typically, this process is conducted at temperatures in the range of about from 0° to 100° C., preferably 20° to 45° C., using about from 1.0 to 4.0 moles of dialkyl sulfate per mole of Compound I. An excess, typically about 2.5 mole of base is used. Preferably, this process is also conducted in an inert organic solvent such as, for example, methylene chloride, carbon tetrachloride, dichloroethane, tetrahydrofuran, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The compatible salts of Formula (I) can be prepared by conventional procedures for example by treating the compound of Formula (I) wherein $R^1$ and/or $R^2$ are hydrogen with a suitable strong base such as, for example, n-butyllithium, sodium hydride, potassium hydride, and the like, having the desired cation, by conventional procedures to yield the corresponding $R^1$ and/or $R^2$ cation salts. The enolate salts can be prepared by treating the $R^1$ and/or $R^2$ cation salts with base via conventional procedures. The acid addition salts can be prepared by treating the free base of Formula (I) with a strong acid. Preferably the free base of Formula (I) is contacted with the strong acid as an anhydrous gas. Suitable acids include, for example, hydrogen fluoride, hydrogen chloride, hydrogen iodide, hydrogen bromide, sulfuric acid and the like. Additional variations in the salt can also be effected via ion exchange with an ion exchange resin having the desired exchange ion.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

DEFINITIONS

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "alkylene" refers to both straight chained and branched chained alkylene groups and includes, for example, —CH$_2$—; —CH$_2$—CH$_2$—;

$$-CH_2-; -CH-CH_2-; -\overset{CH_3}{\underset{|}{C}}H_2CH_2-$$

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR''— wherein R' and R'' are independently straight chain or branched chain alkyl groups having 1 through 3 carbon atoms.

The term "lower alkylthioalkyl" refers to the group R'SR''— wherein R' and R'' are independently straight chain or branched chain alkyl groups having 1 through 3 carbon atoms.

The term "lower alkoxycarbonylalkyl" refers to the group

wherein R' is lower alkyl and R'' is alkylene having 1 through 4 carbon atoms and can be straight or branched chained. Typical alkoxycarbonylalkyl groups include for example, —CH$_2$C(O)OCH$_3$; —CH(CH$_3$)-C(O)OC$_2$H$_5$, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "substituted aryl" refers to aryl groups having 1 through 3 substituents independently selected from the group of lower alkyl, lower alkoxy, halonitro, or haloalkyl having 1 through 3 carbon atoms and 1 through 3 halo atoms. Typical substituted aryl groups include, for example, 2-fluorophenyl, 2-chlorophenyl, 2,6-dimethylphenyl, 4-fluorophenyl, 2-methylphenyl, 2-chloro,3-chloromethylphenyl, 2-nitro,5-methylphenyl, 2,6-dichlorophenyl, 3-trifluoromethylphenyl, 2-methoxyphenyl, 2-bromonaphth-1-yl, 3-methoxyinden-1-yl, and the like.

The term "arylalkylene" refers to the group ArR$^3$— wherein Ar is aryl and R$^3$ is alkylene having 1 through 3 carbon atoms and includes both straight-chained and branched-chained alkylenes, for example, methylene, ethyl, 1-methylethyl, and propyl.

The term "(substituted aryl)alkylene" or "ring-substituted arylalkylene" refers to the group Ar'R$^3$— wherein Ar' is substituted aryl and R$^3$ is alkylene as defined with respect to arylalkylene.

The term "saturated nitrogen heterocycle" as used herein with respect to $R^1$ and $R^2$ of formula I refers to the groups having the formula:

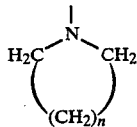

wherein n is 2, or 3.

The term "unsaturated nitrogen heterocycle" as used herein with respect to $R^1$ and $R^2$ of formula I refer to the groups having the formulas:

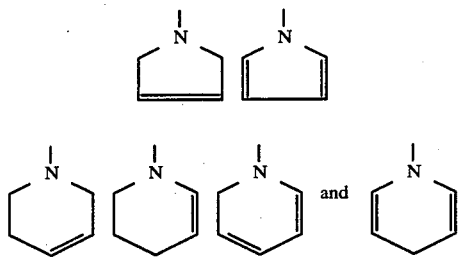

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts; acid addition salts, for example, hydrochloride, hydrobromide, hydrofluoride, hydrosulfate salts and the like.

The term "room temperature" or "ambient temperature" refers to about 20°–25° C.

UTILITY

The compounds of Formula (I) exhibit both pre-emergence and post-emergence herbicidal activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for preemergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages certain of the compounds of the present invention also exhibit plant growth regulating activity, e.g., auxiliary bud growth inhibition, root growth inhibition, and can be used to alter the normal growth pattern of plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

PREPARATION 1

(α-Ethoxycarbonylbenzyl)Acetonitrile

In this example 10 g of ethyl phenylacetate in 10 ml of THF was added dropwise to 61 ml of a 1 molar solution lithium bis[trimethylsilvllamide in tetrahydrofuran, under nitrogen, at −78° C. The mixture was stirred for one hour at −78° C. A solution containing 10.2 g of iodoacetonitrile in 10 ml of tetrahydrofuran was added dropwise. The reaction mixture was stirred at −78° C. for about one-half hour and then stirred for two hours and allowed to warm toward room temperature during this period. The reaction mixture was then added to water and the pH adjusted to pH 1 by the addition of aqueous 10% hydrochloric acid. The mixture was washed with saturated aqueous sodium chloride solution and extracted three times with ethyl ether. The extracts were combined, washed twice with aqueous saturated sodium bicarbonate, dried over magnesium sulfate and evaporated affording 10.7 g of the title compound is an oil. The oil was further purified by chromatography over silica gel eluting with 20% vol. ethyl acetate petroleum ether.

Example 1

[α-(3-Trifluoromethylbenylcarbonyl)Benzyl]Acetonitrile

In this example 42 g of 3-trifluoromethylbenylacetic acid in 100 ml of tetrahydrofuran was added to a cooled slurry containing 9.65 g of sodium hydride in 50 ml of tetrahydrofuran. The resulting mixture was allowed to stand for about 15-18 hours at room temperature, under a nitrogen atmosphere. The mixture was cooled to 0° C. and then 201 ml of a 1 molar solution of lithium bis[-trimethylsilyl]amide in tetrahydrofuran was added. This mixture was stirred for 20 minutes at 0° C. and then 20.4 g of (α-ethoxycarbonylbenzyl)acetonitrile in 50 ml of tetrahydrofuran was added. The mixture was stirred and allowed to warm toward room temperature for 1½ hours, and then added to 1,200 ml of water at room temperature. The aqueous mixture was extracted twice with petroleum ether. The extracts were combined and concentrated under vacuum, to a white paste. The solids were collected by suction filtration and dissolved in methylene chloride. The solution was washed once with aqueous 10% hydrochloric acid; twice with saturated aqueous sodium bicarbonate, dried over magnesium sulfate and evaporated yielding 17.2 g of the title compound as a white solid. 2.2 g of this solid was further purified by recrystallization from methanol, MP 111° to 112° C.

By adapting this procedure using the appropriate starting materials various analogs of the title compound can be prepared.

Example 2

2-(3-Trifluoromethylphenyl)-3-amino-5-phenyl-2-cyclopentenone

A dry 500-ml, three-neck, round-bottomed flask equipped with a mechanical stirrer, addition funnel and a reflux condenser bearing a nitrogen inlet tube was charged with 75 ml of methanol and 4.0 g of sodium. After all the sodium had reacted, a solution containing 38.4 g of [a-(3-trifluoromethyl-benzylcarbonyl)benzyl]acetonitrile in 75 ml of methanol was added rapidly dropwise while the reaction mixture was stirred at reflux. Reflux was continued for about 16 hours after which time the reaction mixture was concentrated in vacuo. The residue was dissolved in diethyl ether and washed once with 10% hydrochloric acid. The aqueous phase was back extracted (2X) with ether and the combined organic layers were dried over magnesium sulfate and concentrated to yield a red paste. The paste was triturated with ether to yield 7.8 g of the title compound as a pale yellow solid, (MP 205° to 206° C.).

Similarly, by adapting the above procedure using the appropriate starting materials, the following compounds can be prepared:

2-(5-chloro-3-trifluoromethylphenyl)-3-amino-5-phenyl-2-cyclopentenone;
2-(4-chloro-3-trifluoromethylphenyl)-3-amino-5-phenyl-2-cyclopentenone;
2-(2-bromo-3-trifluoromethylphenyl)-3-amino-5-phenyl-2-cyclopentenone;
2-(6-fluoro-3-trifluoromethylphenyl)-3-amino-5-phenyl-2-cyclopentenone;
2-(4-methyl-3-trifluoromethylphenyl)-3-amino-5-phenyl-2-cyclopentenone;
2-(5-methoxy-3-trifluoromethylphenyl)-3-amino-5-phenyl-2-cyclopentenone;
2-(6-methyl-3-trifluoromethylphenyl)-3-amino-5-phenyl-2-cyclopentenone;
2-(3,5-di-trifluoromethylphenyl)-3-amino-5-phenyl-2-cyclopentenone;
2-(3-difluoromethoxyphenyl)-3-amino-5-phenyl-2-cyclopentenone;
2-(3-trifluoromethoxyphenyl)-3-amino-5-phenyl-2-cyclopentenone;
2-(3-trifluoromethylphenyl)-3-amino-5-(4-fluorophenyl)-2-cyclopentenone;
2-(3-trifluoromethylphenyl)-3-amino-5-(1-naphthyl)-2-cyclopentenone;
2-(2-chloro-3-methylphenyl)-3-amino-5-phenyl-2-cyclopentenone;
2-(4-ethyl-3-methylphenyl)-3-amino-5-phenyl-2-cyclopentenone;
2-(5-methoxy-3-chlorophenyl)-3-amino-5-phenyl-2-cyclopentenone;
2-(3-iodophenyl)-3-amino-5-phenyl-2-cyclo-pentenone;
2-(3-difluoromethylthiophenyl)-3-amino-5-phenyl-2-cyclopentenone;
2-(3-trifluoromethylthiophenyl)-3-amino-5-phenyl-2-cyclopentenone;
2-(3,5-diethoxyphenyl)-3-amino-5-phenyl-2-cyclopentenone;
2-(3-bromophenyl)-3-amino-5-(2-nitrophenyl)-2-cyclopentenone;
2-(2-chloro-3-methylphenyl)-3-amino-5-phenyl-2-cyclopentenone;
2-(3-bromo-2-ethylphenyl)-3-amino-5-(1-naphthyl)-2-cyclopentenone;
2-(2,3-dimethylphenyl)-3-amino-5-(1-naphthyl)-2-cyclopentenone;
2-(3-chlorophenyl)-3-amino-5-phenyl-2-cyclopentenone;
2-(3-methylphenyl)-3-amino-5-phenyl-2-cyclopentenone;
2-(3-butoxyphenyl)-3-amino-5-phenyl-2-cyclopentenone;

2-(3-propylphenyl)-3-amino-5-phenyl-2-cyclopentenone;
2-(3-bromophenyl)-3-amino-5-phenyl-2-cyclopentenone;
2-(3-iodophenyl)-3-amino-5-(3-nitrophenyl)-2-cyclopentenone;
2-(3-trifluoromethylphenyl)-3-amino-5-(2,3-dichlorophenyl)-2-cyclopentenone;
2-(3-methoxyphenyl)-3-amino-5-(1-naphthyl)-2-cyclopentenone;
2-(3-trifluoromethylphenyl)-3-amino-5-(3-chloro-8-fluoronaphth-1-yl)-2-cyclopentenone;
2-(3-trifluoromethylphenyl)-3-amino-5-(2-trifluoromethyl-3-methyl-8-methoxy-naphth-1-yl)-2cyclopentenone;
2-(3-trifluoromethylphenyl)-3-amino-5-inden-1-yl-2-cyclopentenone;
2-(3-trifluoromethylphenyl)-3-amino-5-(2-fluoroinden-1-yl)-2-cyclopentenone;
2-(3-nitrophenyl)-3-amino-5-phenyl-2-cyclopentenone;
2-(3-cyanophenyl)-3-amino-5-phenyl-2-cyclopentenone;
2-(3-trifluoromethylphenyl)-3-amino-5-methyl-2-cyclopentenone;
2-(3-trifluoromethylphenyl)-3-amino-5-ethyl-2-cyclopentenone;
2-(5-chloro-3-trifluoromethylphenyl)-3-amino-5-ethyl-2-cyclopentenone;
2-(3-trifluoromethylphenyl)-3-amino-5-cyclopentyl-2-cyclopentenone;
2-(3-trifluoromethylphenyl)-3-amino-5-vinyl-2-cyclopentenone;
2-(3-trifluoromethylphenyl)-3-amino-5-allyl-2-cyclopentenone;
2-(2-methoxy-3-trifluoromethylphenyl)-3-amino-5-allyl-2-cyclopentenone;
2-(3-trifluoromethylphenyl)-3-amino-5-trifluoromethyl-2-cyclopentenone;
2-(3-difluoromethoxyphenyl)-3-amino-5-methyl-2-cyclopentenone;
2-(3-trifluoromethoxyphenyl)-3-amino-5-methyl-2-cyclopentenone;
2-(3-trifluoromethylphenyl)-3-amino-5-(2-chlorovinyl)-2-cyclopentenone;
2-(5-propoxy-3-trifluoromethylphenyl)-3-amino-5-(2-chlorovinyl)-2-cyclopentencne;
2-(2-methoxy-3-chlorophenyl)-3-amino-5-methyl-2-cyclopentenone;
2-(2-chloro-3-fluorophenyl)-3-amino-5-ethyl-2-cyclopentenone;
2-(3-methyl-4-methoxyphenyl)-3-amino-5-vinyl-2-cyclopentenone;
2-(3,6-dimethylphenyl)-3-amino-5-allyl-2-cyclopentenone;
2-(3-trifluoromethyl-4-bromophenyl)-3-amino-5-trifluoromethyl-2-cyclopentenone;
2-(3-nitro-4-methylphenyl)-3-amino-5-(2-chlorovinyl)-2-cyclopentenone;
2-(3-methoxyphenyl)-3-amino-5-methyl-2-cyclopentenone;
2-(3-difluoromethylthiophenyl)-3-amino-5-methyl-2-cyclopentenone;
2-(3-trifluoromethylthiophenyl)-3-amino-5-methyl-2-cyclopentenone;
2-(3-chlorophenyl)-3-amino-5-ethyl-2-cyclopentenone;
2-(3-methylphenyl)-3-amino-5-vinyl-2-cyclopentenone;
2-[3,5-di(trifluoromethyl)-phenyl]-3-amino-5-allyl-2-cyclopentenone;
2-(4-fluorophenyl)-3-amino-5-trifluoromethyl-2-cyclopentenone;
2-(2-bromophenyl)-3-oxo-3-amino-5-(2-chlorovinyl)-2-cyclopentenone;
2-(2-methoxy-3-chlorophenyl)-3-amino-5-propyl-2-cyclopentenone;
2-(2-chloro-3-fluorophenyl)-3-amino-5-butyl-2-cyclopentenone;
2-(3-chloro-4-methoxyphenyl)-3-amino-5-vinyl-2-cyclopentenone;
2-(3,5-dimethylphenyl)-3-amino-5-allyl-2-cyclopentenone;
2-(3-trifluoromethyl-5-bromophenyl)-3-amino-5-(trifluoromethyl)-2-cyclopentenone;
2-(3-fluoro-4-methylphenyl)-3-oxo-3-amino-5-(2-chlorovinyl)-2-cyclopentenone;
2-(3-methoxyphenyl)-3-amino-5-phenyl-2-cyclopentenone;
2-(3,5-difluorophenyl)-3-amino-5-methyl-2-cyclopentenone;
2-(3,5-diethylphenyl)-3-amino-5-vinyl-2-cyclopentenone;
2-(3-propoxyphenyl)-3-amino-5-allyl-2-cyclopentenone;
2-(3-fluorophenyl)-3-amino-5-trifluoromethyl-2-cyclopentenone;
2-(3-bromophenyl)-3-oxo-3-amino-5-propyl-2-cyclopentenone;
2-(2-iodo-3-fluorophenyl)-3-amino-5-phenyl-2-cyclopentenone;
2-(2-isopropoxy-3-trifluoromethylphenyl)-3-amino-5-benzyl-2-cyclopentenone;
2-(2,3-dimethylphenyl)-3-amino-5-(3-chlorophenyl)-2-cyclopentenona;
2-(3-trifluoromethyl-4-bromophenyl)-3-amino-5-naphth-1-yl-2-cyclopentenone;
2-(3-butyl-4-methylphenyl)-3-oxo-3-amino-5-(3-methylphenyl)-2-cyclopentenone;
2-(3-chlorophenyl)-3-amino-5-(3-fluorophenyl)-2-cyclopentenone;
2-(3-trifluoromethylphenyl)-3-amino-5-(2,3,5-trifluorophenyl)-2-cyclopentenone;
2-(3-trifluoromethylphenyl)-3-amino-5-(3-methylnapth-1-yl)-2-cyclopentenone;
2-(3-trifluoromethylphenyl)-3-amino-5-(2'-chlorovinyl-2-cyclopentenone;
2-(3-trifluoromethylphenyl)-3-amino-5-fluoromethyl-2-cyclopentenone;
2-(3-trifluoromethylphenyl)-3-amino-5-methoxymethylene-2-cyclopenterone;
2-(3-trifluoromethylphenyl)-3-amino-5-propoxymethylene-2-cyclopentenone;
2-(3-trifluoromethylphenyl)-3-amino-5-ethoxymethylene-2-cyclopentenone;
2-(3-trifluoromethylphenyl)-3-amino-5-(2-methoxypropyl)-2-cyclopentenone;
2-(3-trifluoromethylphenyl)-3-amino-5-methylthiomethylene-2-cyclopentenone;
2-(3-trifluoromethylphenyl)-3-amino-5-(1-propylthioethyl)-2-cyclopentenone;
2-(3-nitrophenyl)-3-amino-5-methyl-2-cyclopentenone;
2-(3-cyanophenyl)-3-amino-5-ethyl-2-cyclopentenone;
2-(3-trifluoromethylphenyl)-3-amino-5-(2-thienyl)-2-cyclopentenone;
2-(3-trifluoromethylphenyl)-3-amino-5-(3-thienyl)-2-cyclopentenone;
2-(3-trifluoromethylphenyl)-3-amino-5-(2-furyl)-2-cyclopentenone;

2-(3-trifluoromethylphenyl)-3-amino-5-(3-furyl)-2-cyclopentenone;
2-(3-chlorophenyl)-3-amino-5-(2-thienyl)-2-cyclopentenone;
2-(3-chlorophenyl)-3-amino-5-(3-thienyl)-2-cyclopentenone;
2-(3-chlorophenyl)-3-amino-5-(2-furyl)-2-cyclopentenone; and
2-(3-chlorophenyl)-3-amino-5-(3-furyl)-2-cyclopentenone.

Example 3

2-(3-Trifluoromethylphenyl)-3-Methylamino-5-Phenyl-2-Cyclopentenone

A 200-ml, round-bottomed flask containing a magnetic stirring bar was charged with 7.8 g of 2-(3-trifluoromethyl)-3-amino-5-phenyl-2-cyclopentenone, 70 ml of methylene chloride, 0.3 g of benzyltriethylammonium chloride and a solution of 1.0 g of sodium hydroxide in 6.0 ml of water. To the resulting stirred mixture was added 2.8 ml (3.7 g) of dimethylsulfate in 10 ml of methylene chloride slowly dropwise. The resulting mixture was stirred for 16 hr. at room temperature after which time it was washed (3X) with water, dried over magnesium sulfate and concentrated in vacuo to yield a dark oil. This oil was triturated with a mixture of diethyl ether/petroleum ether/ethylacetate to afford 2.3 g of the title compound as a white solid.

Similarly, by adapting the above procedure using the products listed in Example 2 as starting materials, the corresponding 5-methylamino homologs thereof can be prepared:
2-(5-chloro-3-trifluoromethylphenyl)-3-methylamino-5-phenyl-2-cyclopentenone;
2-(4-chloro-3-trifluoromethylphenyl)-3-methylamino-5-phenyl-2-cyclopentenone;
2-(2-bromo-3-trifluoromethylphenyl)-3-methylamino-5-phenyl-2-cyclopentenone;
2-(6-fluoro-3-trifluoromethylphenyl)-3-methylamino-5-phenyl-2-cyclopentenone;
2-(4-methyl-3-trifluoromethylphenyl)-3-enyl-2-cyclopentenone;
2-(5-methoxy-3-trifluoromethylphenyl)-3-methylamino-5-phenyl-2-cyclopentenone;
2-(6-methyl-3-trifluoromethylphenyl)-3-methylamino-5-phenyl-2-cyclopentenone;
2-(3,5-di-trifluoroamethylphenyl)-3-methylamino-5-phenyl-2-cyclopentenone,
2-(3-difluoromethylphenyl)-3-methylamino-5-phenyl-2-cyclopentenone;
2-(3-trifluoromethoxyphenyl)-3-methylamino-5-phenyl-2-cyclopentenone;
2-(3-trifluoromethylphenyl)-3-methylamino-5-(4-fluorophenyl)-2-cyclopentenone;
2-(3-trifluoromethylphenyl)-3-methylamino-5-(1-naphthyl)-2-cyclopentenone;
2-(2-chloro-3-methylphenyl)-3-methylamino-5-phenyl-2-cyclopentenone;
2-(4-ethyl-3-methylphenyl)-3-methylamino-5-phenyl-2-cyclopentenone;
2-(5-methoxy-3-chlorophenyl)-3-methylamino-5-phenyl-2-cyclopentenone;
2-(3-iodophenyl)-3-methylamino-5-phenyl-2-cyclopentenone;
2-(3-difluoromethylthiophenyl)-3-methylamino-5-phenyl-2-cyclopentenone;
2-(3-trifluoromethylthiophenyl)-3-methylamino-5-2-(3,5-diethoxyphenyl)-3-methylamino-5-phenyl-2-cyclopentenone;
2-(3-bromophenyl)-3-methylamino-5-(2-nitrophenyl)-2-cyclopentenone;
2-(2-chloro-3-methylphenyl)-3-methylamino-5-phenyl-2-cyclopentenone;
2-(3-bromo-2-ethylphenyl)-3-methylamino-5-(1-naphthyl)-2-cyclopentenone;
2-(2,3-dimethylphenyl)-3-methylamino-5-(1-naphthyl)-2-cyclopentenone;
2-(3-chlorophenyl)-3-methylamino-5-phenyl-2-cyclopentenone;
2-(3-methylphenyl)-3-methylamino-5-phenyl-2-cyclopentenone;
2-(3-butoxyphenyl)-3-methylamino-5-phenyl-2-cyclopentenone;
2-(3-propylphenyl)-3-methylamino-5-phenyl-2-cyclopentenone;
2-(3-bromophenyl)-3-methylamino-5-phenyl-2-cyclopentenone;
2-(3-iodophenyl)-3-methylamino-5-(3-nitrophenyl)-2-cyclopentenone;
2-(3-trifluoromethylphenyl)-3-methylamino-5-(2,3-dichlorophenyl)-2-cyclopentenone;
2-(3-methoxyphenyl)-3-methylamino-5-(1-naphthyl)-2-cyclopentenone;
2-(3-trifluoromethylphenyl)-3-methylamino-5-(3-chloro-8-fluoronaphth-1-yl)-2-cyclopentenone;
2-(3-trifluoromethylphenyl)-3-methylamino-5-(2-trifluoromethyl-3-methyl-8-methoxy-naphth-1-yl)-2-cyclopentenone;
2-(3-trifluoromethylphenyl)-3-methylamino-5-inden-1-yl-2-cyclopentenone;
2-(3-trifluoromethylphenyl)-3-methylamino-5-(2-fluoroinden-1-yl)-2-cyclopentenone;
2-(3-nitrophenyl)-3-methylamino-5-phenyl-2-cyclopentenone;
2-(3-cyanophenyl)-3-methylamino-5-phenyl-2-cyclopentenone;
2-(3-trifluoromethylphenyl)-3-methylamino-5-methyl-2-cyclopentenone;
2-(3-trifluoromethylphenyl)-3-methylamino-5-ethyl-2-cyclopentenone;
2-(5-chloro-3-trifluoromethylphenyl)-3-methylamino-5-ethyl-2-cyclopentenone;
2-(3-trifluoromethylphenyl)-3-methylamino-5-cyclopentyl-2-cyclopentenone;
2-(3-trifluoromethylphenyl)-3-methylamino-5-allyl-2-cyclopentenone;
2-(2-methoxy-3-trifluoromethylphenyl)-3-methylamino-5-allyl-2-cyclopentenone;
2-(3-trifluoromethylphenyl)-3-methylamino-5-trifluoromethyl-2-cyclopentenone;
2-(3-difluoromethoxyphenyl)-3-methylamino-5-methyl-2-cyclopentenone;
2-(3-trifluoromethoxyphenyl)-3-methylamino-5-methyl-2-cyclopentenone;
2-(3-trifluoromethylphenyl)-3-methylamino-5-(2-chlorovinyl)-2-cyclopentenone;
2-(5-propoxy-3-trifluoromethylphenyl)-3-methylamino-5-(2-chlorovinyl)-2-cyclopentenone;
2-(2-methoxy-3-chlorophenyl)-3-methylamino-5-methyl-2-cyclopentenone;
2-(2-chloro-3-fluorophenyl)-3-methylamino-5-ethyl-2-cyclopentenone;
2-(3-methyl-4-methoxyphenyl)-3-methylamino-5-vinyl-2-cyclopentenone;

2-(3,6-dimethylphenyl)-3-methylamino-5-allyl-2-cyclopentenone;
2-(3-trifluoromethyl-4-bromophenyl)-3-methylamino-5-trifluoromethyl-2-cyclopentenone;
2-(3-nitro-4-methylphenyl)-3-methylamino-5-(2-chlorovinyl)-2-cyclopentenone;
2-(3-methoxyphenyl)-3-methylamino-5-methyl-2-cyclopentenone;
2-(3-difluoromethylthiophenyl)-3-methylamino-5-methyl-2-cyclopentenone;
2-(3-trifluoromethylthiophenyl)-3-methylamino-5-methyl-2-cyclopentenone;
2-(3-chlorophenyl)-3-methylamino-5-ethyl-2-cyclopentenone;
2-(3-methylphenyl)-3-methylamino-5-vinyl-2-cyclopentenone;
2-[3,5-di(trifluoromethyl)-phenyl]-3-methylamino-5-allyl-2-cyclopentenone;
2-(4-fluorophenyl)-3-methylamino-5-trifluoromethyl-2-cyclopentenone;
2-(2-bromophenyl)-3-oxo-3-methylamino-5-(2-chlorovinyl)-2-cyclopentenone;
2-(2-methoxy-3-chlorophenyl)-3-methylamino-5-propyl-2-cyclopentenone;
2-(2-chloro-3-fluorophenyl)-3-methylamino-5-butyl-2-cyclopentenone;
2-(3-chloro-4-methoxyphenyl)-3-methylamino-5-vinyl-2-cyclopentenone;
2-(3,5-dimethylphenyl)-3-methylamino-5-allyl-2-cyclopentenone;
2-(3-trifluoromethyl-5-bromophenyl)-3-methylamino-5-(trifluoromethy)-2-cyclopentenone;
2-(3-fluoro-4-methylphenyl)-3-oxo-3-methylamino-5-(2-chlorovinyl)-2-cyclopentenone;
2-(3-methoxyphenyl)-3-methylamino-5-phenyl-2-cyclopentenone;
2-(3,5-difluorophenyl)-3-methylamino-5-methyl-2-cyclopentenone;
2-(3,5-diethylphenyl)-3-methylamino-5-vinyl-2-cyclopentenone;
2-(3-propoxyphenyl)-3-methylamino-5-allyl-2-cyclopentenone;
2-(3-fluorophenyl)-3-methylamino-5-yl-2-cyclopentenone;
2-(3-bromophenyl)-3-oxo-3-methylamino-5-propyl-2-cyclopentenone;
2-(2-iodo-3-fluorophenyl)-3-methylamino-5-phenyl-2-cyclopentenone;
2-(2-isopropoxy-3-trifluoromethylphenyl)-3-methylamino-5-benzyl-2-cyclopentenone;
2-(2,3-dimethylphenyl)-3-methylamino-5-(3-chlorophenyl)-2-cyclopentenone;
2-(3-trifluoromethyl-4-bromophenyl)-3-methylamino-5-naphth-1-yl-2-cyclopentenone;
2-(3-butyl-4-methylphenyl)-3-oxo-3-methylamino-5-(3-methylphenyl)-2-cyclopentenone;
2-(3-chlorophenyl)-3-methylamino-5-(3-fluorophenyl)-2-cyclopentenone;
2-(3-trifluoromethylphenyl)-3-methylamino-5-(2,3,5-trifluorophenyl)-2-cyclopentenone;
2-(3-trifluoromethylphenyl)-3-methylamino-5-(3-methylnapth-1-yl)-2-cyclopentenone;
2-(3-trifluoromethylphenyl)-3-methylamino-5-(2'-chlorovinyl-2-cyclopentenone;
2-(3-trifluoromethylphenyl)-3-methylamino-5-fluoromethyl-2-cyclopentenone;
2-(3-trifluoromethylphenyl)-3-methylamino-5-methoxymethylene-2-cyclopentenone;
2-(3-trifluoromethylphenyl)-3-methylamino-5-propoxymethylene-2-cyclopenterone;
2-(3-trifluoromethylphenyl)-3-methylamino-5-ethoxymethylene-2-cyclopentencne;
2-(3-trifluoromethylphenyl)-3-methylamino-5-(2-methoxypropyl)-2-cyclopentenone;
2-(3-trifluoromethylphenyl)-3-methylamino-5-methylthiomethylene-2-cyclopentenone;
2-(3-trifluoromethylphenyl)-3-methylamino-5-(1-propylthioethyl)-2-cyclopentenone;
2-(3-nitrophenyl)-3-methylamino-5-methyl-2-cyclopentenone;
2-(3-cyanophenyl)-3-methylamino-5-ethyl-2-cyclopentenone;
2-(3-trifluoromethylphenyl)-3-methylamino-5-(2-thienyl)-2-cyclopentenone;
2-(3-trifluoromethylphenyl)-3-methylamino-5-(3-thienyl)-2-cyclopentenone;
2-(3-trifluoromethylphenyl)-3-methylamino-5-(2-furyl)-2-cyclopentenone;
2-(3-trifluoromethylphenyl)-3-methylamino-5-(3-furyl)-2-cyclopentenone;
2-(3-chlorophenyl)-3-methylamino-5-(2-thienyl)-2-cyclopentenone;
2-(3-chlorophenyl)-3-methylamino-5-(3-thienyl)-2-cyclopentenone;
2-(3-chlorophenyl)-3-methylamino-5-(2-furyl)-2-cyclopentenone; and
2-(3-chlorophenyl)-3-methylamino-5-(3-furyl)-2-cyclopentenone.

Similarly, by approximately doubling the amount of dimethylsulfate and increasing the reaction time, the corresponding 5-dimethylamino homologs of the above compounds can be prepared. Similarly, by using diethylsulfate in place of dimethylsulphate the corresponding 5-ethylamino and 5-diethylamiro homologs of the above compounds can be prepared.

Example 4

2-(3-Trifluoromethylphenyl)-3-Ethylamino-5-PropyI-2-Cyclopentenone

In this example, a mixture containing 8.0 g of 2-(3-trifluoromethylphenyl)-3-amino-5-propyl-2-cyclopentenone; 3.0 g of aqueous 50 wt % sodium hydroxide; 6.4 g of benzyltriethylammonium chloride; and 5.0 ml of diethyl sulfate in 70 ml of methylene chloride was stirred at room temperature for about 1 hour and then warmed to, and stirred at reflux for about 15 to 20 minutes. The mixture was cooled to room temperature and successively washed three times with water, twice with aqueous 1N hydrochloric acid and then twice with saturated aqueous sodium bicarbonate. The washed mixture was dried over magnesium sulfate and evaporated affording an oil residue. The oil was triturated with a mixture of ethyl ether and petroleum ethers and filtered affording 3.2 g of the title compound as a solid, m.p. 120°–120.5° C.

The filtrate from the trituration was allowed to stand for about 3 days at room temperature resulting in its solidification. The solidified filtrate was then triturated with ethyl ether and petroleum ethers. 3.3 g of solids were collected from the trituration by filtration. The filtrate was evaporated affording another 2.9 g of solids. The solids were combined with 3.0 g of benzyltriethylammonium chloride, 2.5 ml of diethyl sulfate and 1.5 g of aqueous 50 wt % sodium hydroxide in methylene chloride and refluxed for about 1½ hours. The reaction mixture was cooled to room temperature and washed twice with aqueous 1N hydrochloric acid and twice with saturated aqueous sodium bicarbonate. The washed mixture was dried over magnesium sulfate and evaporated yielding an oil. The oil was triturated with a mixture of ethyl ether and petroleum ethers. The solids were collected by filtration yielding another 2.8 g of the title compound as a powder.

Similarly by applying the same procedure using the products listed in Example 2 as starting materials the corresponding 5-ethylamino analog can be prepared, for example;

2-(3-trifluoromethylphenyl)-3-ethylamino-5-phenyl-2-cyclopentenone;
2-(3-trifluoromethylphenyl)-3-ethylamino-5-ethyl-2-cyclopentenone;
2-(3-trifluoromethylphenyl)-3-ethylamino-5-(1-naphthyl)-2-cyclopentenone;
2-(3-trifluoromethylphenyl)-3-ethylamino-5-allyl-2-cyclopentenone;
2-(3-trifluoromethylphenyl)-3-ethylamino-5-methoxymethylene-2-cyclopenterone; etc.

Example 4A

2-(3-Trifluoromethylphenyl-3-Ethylamino-5-Propyl-2-Cyclopentenone

In this example a mixture containing 1.1 g of 2-(3-trifluoromethylphenyl)-3-amino-5-propyl-2-cyclopentenone; 0.93 g of aqueous 50 wt % sodium hydroxide; 2.02 g of benzyltriethylammonium chloride; and 1.8 g of diethyl sulfate in 15 ml of methylene chloride was stirred at room temperature for about 1½ hours. The mixture was successively washed three times with water, twice with aqueous 1N hydrochloric acid and then twice with saturated aqueous sodium bicarbonate. The washed mixture was dried over magnesium sulfate and evaporated affording an oil residue. The oil was triturated with a mixture of ethyl ether and petroleum ethers and filtered affording 0.6 g of the title compound as a solid, m.p. 120°–124° C.

Example 5

2-(3-Trifluoromethylphenyl)-3-Allylamino-5-Phenyl-2-Cyclopentenone

The title compound can be prepared by the following procedure.

One gram of sodium hydroxide in 4.0 ml of water is added to a mixture of 4.0 g of 2-(3-trifluoromethylphenyl)-3-amino-5-phenyl-2-cyclopentenone in 80 ml of methylene chloride at room temperature followed by the addition of 1.46 g of allyl bromide and 0.27 g of benzyltriethylammonium chloride. The resulting two-phase mixture is stirred at room temperature until the reaction is completed. The reaction mixture is washed three times with water, dried over magnesium sulfate and concentrated in vacuo. The residue is typically purified by chromatography to yield the title compound.

Similarly, by applying this procedure to the products listed in Examples 2, the corresponding -allylamino analogs thereof can be prepared. Similarly, by approximately doubling the amount of allyl bromide and sodium hydroxide, the corresponding 5-diallylamino analogs thereof can be prepared.

In a like manner, by using ethyl bromide in place of allyl bromide, the corresponding 5-ethylamino and 5-diethylamino analogs can be prepared.

Similarly, by following the same procedure by respectively using methoxymethyl bromide, ethylthiomethyl bromide, methyl bromoacetate, methyl 2-bromobutyrate, 1,5-dibromopentane, and cis-1,4-dibromobut-1,3-diene in place of alkyl bromide the corresponding 5-methoxymethylamino, 5-ethylthiomethylamino, 5-methoxycarbonylmethylamino, 5-(1-methoxycarbonylpropylamino), 5-piperidin-1-yl and 5-pyrrol-1-yl analogs of the products listed in Example 2 can be prepared for example:

2-(3-trifluoromethylphenyl)-3-methoxymethylamino-5-phenyl-2-cyclopentenone;
2-(3-trifluoromethylphenyl)-3-methoxymethylamino-5-methyl-2-cyclopentenone;
2-(3-trifluoromethylphenyl)-3-methoxymethylamino-5-ethyl-2-cyclopentenone;
2-(3-trifluoromethylphenyl)-3-ethylthiomethylamino-5-phenyl-2-cyclopentenone;
2-(3-trifluoromethylphenyl)-3-ethylthiomethylamino-5-methoxy-2-cyclopentenone;
2-(3-trifluoromethy-phenyl)-3-ethylthiomethylamino-5-methyl-2-cyclopentenone;
2-(3-trifluoromethylphenyl)-3-ethylthiomethylamino-5-ethoxymethylene-2-cyclopentenone;
2-(3-trifluoromethylphenyl)-3-ethylthiomethylamino-5-ethyl-2-cyclopentenone;
2-(3-trifluoromethylphenyl)-3-methoxycarbonylmethylamino-5-phenyl-2-cyclopentenone;
2-(3-trifluoromethylphenyl)-3-methoxycarbonylmethylamino-5-methyl-2-cyclopentenone;
2-(3-trifluoromethylphenyl)-3-methoxycarbonylmethylamino-5-methylthiomethylene-2-cyclopentenone;
2-(3-trifluoromethylphenyl)-3-methoxycarbonylmethylamino-5-ethyl-2-cyclopertenone;
2-(3-trifluoromethylphenyl)-3-(1-methoxycarbonyl-prop-1-yl)amino-5-phenyl-2-cyclopentenone;
2-(3-trifluoromethylphenyl)-3-(1-methoxycarbonyl-prop-1-yl)amino-5-methyl-2-cyclopentenone;
2-(3-trifluoromethylphenyl)-3-(1-methoxycarbonyl-prop-1-yl)amino-5-fluoro-2-cyclopentenone;
2-(3-trifluoromethylphenyl)-3-(1-methoxycarbonyl-prop-1-yl)amino-5-ethyl-2-cyclopentenone;
2-(3-trifluoromethylphenyl)-3-(1-methoxycarbonyl-prop-1-yl)amino-5-naphth-1-yl-2-cyclopentenone;
2-(3-trifluoromethylphenyl)-3-(1-methoxycarbonyl-prop-1-yl)amino-5-inden-1-yl-2-cyclopentenone;
2-(3-trifluoromethylphenyl)-3-piperidin-1-yl-5-phenyl-2-cyclopentenone; and
2-(3-trifluoromethylphenyl)-3-pyrrol-1-yl-5-phenyl-2-cyclopentenone;
2-(3-trifluoromethylphenyl)-3methoxymethylamino-5-(2-thienyl)-2-cyclopentenone;
2-(3-trifluoromethylphenyl)-3-ethylthiomethylamino-5-(3-thienyl)-2-cyclopentenone;
2-(3-trifluoromethylphenyl)-3-methoxycarbonylmethylamino-5-(2-furyl)-2-cyclopentenone;
2-(3-trifluoromethylphenyl)-3-methoxycarbonylprop-1-yl)amino-5-(3-furyl)-2-cyclopentenone;
2-(3-chlorophenyl)-3-piperidin-1-yl-5-(2-thienyl)-2-cyclopentenone;
2-(3-chlorophenyl)-3-pyrrol-1-yl-5-(3-thienyl)-2-cyclopentenone;
2-(3-chlorophenyl)-3-methoxymethylamino-5-(2-furyl)-2-cyclopentenone; and
2-(3-chlorophenyl)-3-ethylthiomethylamino-5-(3-furyl)-2-cyclopentenone.

Similarly, by applying the above procedures using the 5-methylamino produrts of Example 3 as starting materials, the corresponding 5-(N-methyl-N-allylamino), 5-(N-methyl-N-ethylamino), 5-(N-methyl-N-methoxymethylamino), 5-(N-methyl-N-ethylthiomethylamino), 5-(N-methyl-N-methoxycarbonylmethylamino), and 5-(N-methyl-N-1'-methoxycarbonylpropylamino) analogs can be prepared.

Example 6

Lithium salt of 2-(3-Trifluoromethylphenyl)-3-Methylamino-5-Phenyl-2-Cyclopentenone ($R^1$=—$CH_3$, $R^2$=Li)

This example illustrates a procedure which can be adapted to prepare the lithium salts of the invention.

5.4 ml of 1.6M n-butyllithium in hexane is added dropwise to a stirred solution containing 2.83 g of 2-(3-trifluoromethylphenyl)-3-methylamino-4-phenyl-2-cyclopentenone in 25 ml of tetrahydrofuran at $-30°$ C. The resulting mixture is stirred until the reaction is complete. The title compound can be collected by evaporation off the solvent.

Similarly, by adapting the above procedure, the corresponding lithium salts of the compounds of Examples 2–5 can also be prepared.

Example 7

Hydrobromide addition salt of 2-(3-trifluoromethylphenyl)-3-amino-4-phenyl-2-cyclopentenone This example illustrates a procedure which can be adapted to prepare the hydrobromide addition salts of the invention.

Gaseous hydrogen bromide is bubbled into a slurry containing 2.32 g (0.007 mole) of 2-(3-trifluoromethylphenyl)-3-amino-4-phenyl-2-cyclopentenone in 35 ml of methylene chloride at room temperature. The addition of hydrogen bromide is discontinued when the reaction is complete. The title compound can be collected by evaporating off the solvent.

Similarly, by adapting the above procedure the corresponding hydrobromide addition salts of the compounds of Examples 2–5 can be prepared.

Example 8

The compounds listed in the tables hereinbelow were prepared using the appropriate starting materials and the appropriate procedures described hereinabove.

TABLE A

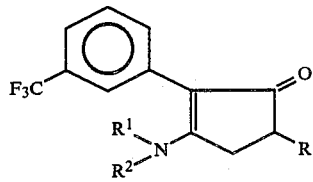

| No. | R | $R^1$ | $R^2$ | Melting Point °C. |
|---|---|---|---|---|
| 1 | H | H | H | 136–137* |
| 2 | $CH_3$ | H | H | 109–110 |
| 3 | $C_2H_5$ | H | H | 139 |
| 4 | $C_2H_5$ | $CH_3$ | H | 133–138 |
| 5 | $(CH_2)_2CH_3$ | H | H | 162 |
| 6 | $(CH_2)_2CH_3$ | $CH_3$ | H | oil |
| 7 | $(CH_2)_2CH_3$ | $C_2H_5$ | H | 120–120.5 |
| 8 | φ** | H | H | 205–206 |
| 9 | φ | $CH_3$ | H | 146–148 |

TABLE A-continued

| No. | R | $R^1$ | $R^2$ | Melting Point °C. |
|---|---|---|---|---|
| 10 | φ | $CH_3$ | $CH_3$ | 60–64 |
| 11 | φ | $C_2H_5$ | H | 127–129 |
| 12 | 2-$CH_3$φ | H | H | 170–171 |
| 13 | 2-$CH_3$φ | $CH_3$ | H | 130–137 |
| 14 | 2-Fφ | H | H | 214–216* |
| 15 | 2-Fφ | $CH_3$ | H | 160–170 |
| 16 | 2-Clφ | H | H | 166–166.5 |
| 17 | 2-Clφ | $CH_3$ | H | 155–163 |
| 18 | 3-Clφ | H | H | 149–150 |
| 19 | 3-Clφ | $CH_3$ | H | 134–137 |
| 20 | 4-Clφ | H | H | 195–197* |
| 21 | 4-Clφ | $CH_3$ | H | 76–83 |
| 22 | 3-thienyl | H | H | 158–161 |

*Decomposition temperature
φ**Phenyl, for example, 2-Clφ = 2-chlorophenyl

TABLE B
COMPARISON COMPOUNDS

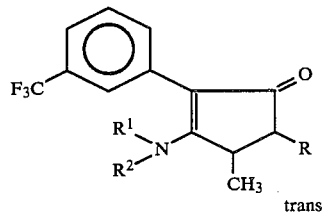

trans

| No. | R | $R^1$ | $R^2$ | Melting Point °C. |
|---|---|---|---|---|
| C-1 | φ | H | H | 203–206* |
| C-2 | φ | $CH_3$ | H | 152–165 |

*Decomposition temperature

Example 9

In this example, the compounds tabulated in the preceding tables were respectively tested for pre-emergent and post-emergent activity against a variety of grasses and broad-leaf plants including one grain crop and one broad-leaf crop using the procedures described hereinbelow. The compounds tested are identified by compound number in the tables hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/cm$^2$ or in some instances as indicated in Table 1 hereinbelow, certain cf the compounds were tested at a lower dosage of 15.6 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm$^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1

Pre-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 60 | 50 | 40 | 70 | 50 | 65 | 100 | 70 |
| 2 | 75 | 95 | 70 | 90 | 100 | 100 | 100 | 98 |
| 3 | 100 | 100 | 100 | 99 | 100 | 100 | 100 | 100 |
| 4 | 100 | 100 | 100 | 99 | 100 | 100 | 100 | 100 |
| 5 | 100 | 100 | 99 | 80 | 100 | 100 | 99 | 99 |
| 6 | 100 | 100 | 100 | 98 | 100 | 100 | 100 | 100 |
| 7 | 100 | 100 | 100 | 80 | 100 | 100 | 100 | 100 |
| 8 | 100 | 100 | 100 | 100 | 100 | 100 | 100 | 100 |
| 9 | 100 | 100 | 100 | 100 | 100 | 100 | 100 | 100 |
| 10 | 25 | 0 | 15 | 0 | 0 | 0 | 0 | 0 |
| 11 | 100 | 100 | 100 | 100 | 100 | 100 | 100 | 100 |
| 12 | 99 | 98 | 99 | 83 | 100 | 98 | 89 | 90 |
| 13 | 100 | 100 | 100 | 100 | 100 | 100 | 100 | 100 |
| 14 | 100 | 100 | 100 | 100 | 100 | 100 | 100 | 100 |
| 15 | 100 | 100 | 100 | 100 | 100 | 100 | 100 | 100 |
| 16 | 100 | 100 | 100 | 100 | 100 | 100 | 100 | 100 |
| 17 | 100 | 100 | 100 | 100 | 100 | 100 | 100 | 100 |
| 18 | 100 | 100 | 100 | 98 | 100 | 100 | 100 | 95 |
| 19 | 100 | 100 | 100 | 99 | 100 | 100 | 100 | 100 |
| 20 | 45 | 30 | 35 | 0 | 25 | 0 | 10 | 0 |
| 21 | 100 | 100 | 100 | 95 | 100 | 97 | 95 | 98 |
| 22 | 100 | 100 | 100 | 100 | 100 | 100 | 100 | 100 |

TABLE 1A

COMPARISON COMPOUNDS
Pre-Emergence Herbicidal Activity
Application Rate: 27.5 micrograms/cm$^2$, unless otherwise noted.

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| C-1 | 0 | 0 | 0 | 0 | 0 | 0 | 0 | 0 |
| C-2 | 0 | NT* | 0 | 0 | 0 | 0 | 0 | 0 |

NT* = Not Tested

The test compound was formulated in the same manner as described above for the pre-emergent test. This

TABLE 2

Post-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 20 | 20 | 20 | 20 | 0 | 0 | 0 | 0 |
| 2 | 35 | 35 | 35 | 30 | 0 | 0 | 0 | 0 |
| 3 | 60 | 98 | 65 | 40 | 40 | 50 | 30 | 0 |
| 4 | 85 | 100 | 85 | 80 | 80 | 90 | 85 | 65 |
| 5 | 50 | 90 | 10 | 30 | 80 | 75 | 94 | 15 |
| 6 | 94 | 100 | 90 | 95 | 95 | 99 | 75 | 58 |
| 7 | 90 | 97 | 50 | 60 | 98 | 98 | 99 | 85 |
| 8 | 50 | 70 | 40 | 35 | 55 | 55 | 25 | 0 |
| 9 | 93 | 100 | 97 | 75 | 90 | 90 | 85 | 55 |
| 10 | 10 | 10 | 25 | 20 | 0 | 0 | 0 | 0 |
| 11 | 95 | 100 | 98 | 95 | 85 | 80 | 75 | 70 |

TABLE 2-continued

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 12 | 50 | 100 | 50 | 40 | 50 | 60 | 60 | 25 |
| 13 | 93 | 100 | 90 | 75 | 60 | 65 | 30 | 25 |
| 14 | 50 | 100 | NT* | 60 | 70 | 55 | 45 | 15 |
| 15 | 98 | 100 | 85 | 75 | 75 | 75 | 30 | 30 |
| 16 | 100 | 100 | 100 | 50 | 70 | 70 | 65 | 50 |
| 17 | 100 | 100 | 100 | 75 | 65 | 55 | 45 | 50 |
| 18 | 55 | 85 | 70 | 45 | 30 | 45 | 20 | 0 |
| 19 | 75 | 93 | 90 | 75 | 80 | 80 | 65 | 40 |
| 20 | 20 | 20 | 20 | 20 | 0 | 0 | 0 | 0 |
| 21 | 90 | 100 | 90 | 75 | 55 | 40 | 40 | 40 |
| 22 | 90 | 100 | 65 | 75 | 80 | 70 | 40 | 25 |

TABLE 2A

COMPARISON COMPOUNDS
Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| C-1 | 0 | 0 | 0 | 0 | 0 | 0 | 0 | 0 |
| C-2 | 0 | 0 | 0 | 0 | 0 | 0 | 0 | 0 |

As can be seen from the above Table 1, the compounds of the invention generally exhibit a broad spectrum of good to excellent pre-emergence phytotoxic activity and especially so Compounds Nos. 3–9, 11, 13–19, 21 and 22. Moreover, as shown by Table 2 the compounds also generally exhibit post-emergence phytotoxic activity against broad-leaf plants and in some instances also against grasses Also, it can be seen that although Comparison Compounds differed from Compound Nos. 8 and 9, respectively, only in the presence of a 4-methyl substituent, the comparison compounds were inactive whereas Compound Nos. 8 and 9 exhibited excellent herbicidal activity. Also as can be seen from Tables 1 and 2 the presence of a single substituent on the exocyclic amine group potentiated activity whereas, based on one example, the presence of two substituents on the exocyclic amine group appeared to detract from activity.

Example 10

In this example Compounds Nos. 6 and 7 (i.e., 2-(3-trifluoromethylphenyl)-3-methylamino-5-propyl-2-cyclopentenone and 2-(3-trifluoromethylphenyl)-3-ethylamino-5-propyl-2-cyclopentenone) were tested at low dosage rates for pre-emergence efficacy against additional weed species and also for safety at these dosage rates for a variety of crops.

These tests were conducted in the same manner as described in Example 9 with the exception that four replicates were run per test and that the dosage rates indicated in Table 3 hereinbelow were used. The results are reported in Table 3 as an average of the four replicates. The plants were visually rated using a 0 to 100 scale wherein 0 indicates no effect and 100 indicates complete kill of the plant.

TABLE 3

| | Compound No. 6[1] Rate γ/cm² | | | | Compound No. 7[2] Rate γ/cm² | | | |
|---|---|---|---|---|---|---|---|---|
| | 4.4 | 1.7 | .70 | .28 | 4.4 | 1.7 | .70 | .28 |
| | % Phytotoxicity | | | | | | | |
| BROADLEAF CROPS | | | | | | | | |
| Peanuts | 8 | 0 | 0 | 0 | 0 | 0 | 0 | 0 |
| Sugar Beets | 100 | 100 | 100 | 76 | 100 | 100 | 98 | 90 |
| Soybean | 86 | 33 | 0 | 0 | 0 | 0 | 0 | 0 |
| Cotton | 0 | 0 | 0 | 0 | 0 | 0 | 0 | 0 |
| Alfalfa | 100 | 60 | 23 | 0 | 70 | 6 | 0 | 0 |
| Peas | 60 | 40 | 10 | 0 | 46 | 5 | 0 | 70 |
| GRASS CROPS | | | | | | | | |
| Oats | 100 | 100 | 71 | 35 | 100 | 100 | 98 | 100 |
| Sorghum (NK125) | 100 | 100 | 73 | 56 | 100 | 100 | 95 | 100 | |
| Anza Wheat | 100 | 100 | 83 | 45 | 100 | 100 | 98 | 100 |
| Field Corn | 100 | 100 | 70 | 41 | 100 | 96 | 76 | 100 |
| BROADLEAF WEEDS | | | | | | | | |
| Velvetleaf | 100 | 90 | 23 | 0 | 100 | 78 | 21 | 0 |
| Field Bindweed | 100 | 100 | 100 | 96 | 100 | 100 | 100 | 96 |
| Jimson Weed | 100 | 90 | 38 | 0 | 100 | 100 | 100 | 76 |
| Prickly Sida | 100 | 93 | 53 | 0 | 100 | 100 | 87 | 61 |
| GRASS WEEDS AND NUTSEDGE | | | | | | | | |
| Cheatgrass | 100 | 91 | 40 | 0 | 100 | 96 | 91 | 90 |
| Yellow Nutsedge | 98 | 93 | 36 | 0 | 100 | 96 | 56 | 99 |

TABLE 3-continued

| | Compound No. 6[1] Rate γ/cm² | | | | Compound No. 7[2] Rate γ/cm² | | | |
|---|---|---|---|---|---|---|---|---|
| | 4.4 | 1.7 | .70 | .28 | 4.4 | 1.7 | .70 | .28 |
| | | | | % Phytotoxicity | | | | |
| Ital. Ryegrass | 100 | 100 | 90 | 30 | 100 | 100 | 100 | 100 |
| Switchgrass | 100 | 100 | 100 | 83 | 100 | 100 | 100 | 100 |
| Yellow Foxtail | 100 | 100 | 100 | 90 | 100 | 100 | 100 | 100 |
| Johnsongrass | 100 | 100 | 100 | 68 | 100 | 100 | 100 | 100 |

[1] 2-(3-trifluoromethylphenyl)-3-methylamino-5-propyl-2-cyclopentenone
[2] 2-(3-trifluoromethylphenyl)-3-ethylamino-5-propyl-2-cyclopentenone
[3] γ/cm² = micrograms/square centimeter.

As can be seen from the above table both compounds exhibited excellent pre-emergence herbicidal activity against both the broadleaf and grassy weeds (including nutsedge) in this test. Moreover, at even the 4.4 γ/cm² rate Compound No. 7 was safe with respect to the major crops of soybean, peanuts and cotton while exhibiting 100% control of the weeds in this test. By lowering the dosage rate to 1.7 γ/cm², Compound No. 7 was also safe with respect to alfalfa and peas. Compound No. 6 was not quite as good in terms of safety as Compound No 7, but, nonetheless was still very good. At 4.4 γ/cm² Compound No. 6 was safe with respect to peanuts and cotton. At 1.7 γ/cm² Compound No. 6 was also borderline safe with respect to soybean and while still retaining very good herbicide properties with respect to the weeds. At 0.70 γ/cm² Compound No. 6 was safe with respect to soybean and peas, and could also be considered safe with respect to alfalfa, though some phytotoxicity was shown. At 0.70 γ/cm² herbicidal activity for Compound No. 6 broke for a number of weeds but nonetheless Compound No. 6 still maintained very good to excellent herbicidal activity against 6 of the 10 weed species tested.

Obviously, many modifications and variations of the invention described hereinabove and below can be made without departing from the essence and scope thereof.

What is claimed is:

1. A compound having the formula:

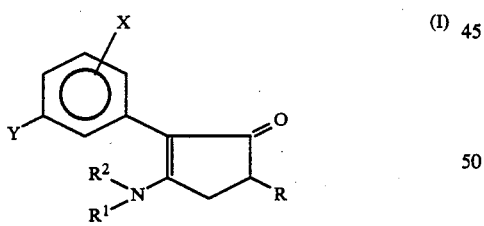

wherein R is lower alkyl, cycloalkyl having 3 through 7 carbon atoms; lower alkenyl; fluoroalkyl having 1 through 4 carbon atoms and 1 through 3 fluorine atoms; haloalkenyl having 2 through 4 carbon atoms and 1 through 3 halo atoms independently selected from the group of fluoro, chloro, bromo, or iodo; lower alkoxyalkyl wherein the alkyl and alkoxy moieties independently have 1 through 3 carbon atoms; alkylthioalkyl wherein the alkyl moieties independently have 1 through 3 carbon atoms; phenyl, naphthyl, inden-1-yl; 4-fluorophenyl; 4-chlorophenyl; thienyl; furyl; arylalkylene having 1 through 3 carbon atoms in the alkylene moiety and wherein the aryl moiety is phenyl, nephth-1-yl or inden-1-yl; or R is a substituted aryl or substituted arylalkylene selected from the group having the formulas:

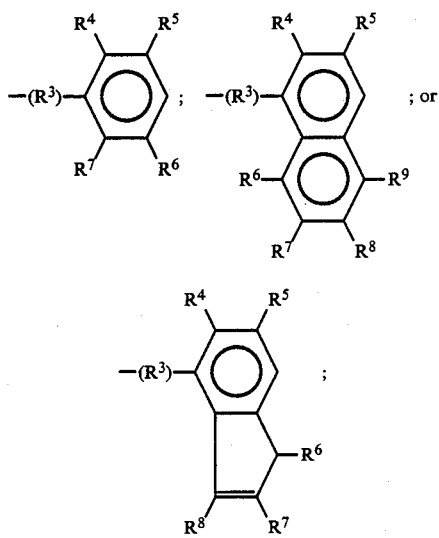

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen; and $R^3$ is a single bond or alkylene having 1 through 3 carbon atoms;

$R^1$ is hydrogen or alkyl having 1 through 4 carbon atoms;

$R^2$ is hydrogen, alkyl having 1 through 4 carbon atoms, alkenyl having 3 or 4 carbon atoms, lower alkoxycarbonylalkyl, lower alkoxyalkyl or lower alklylthioalkyl; or $R^1$ and $R^2$ together with the nitrogen atom to which they are joined form a saturated or unsaturated nitrogen heterocycle having 5 or 6 ring atoms one of which is nitrogen and the remainder are carbon atoms;

X is hydrogen, lower alkyl, lower alkoxy, halo, or trifluoromethyl and can be at any available position on the phenyl ring; and Y is lower alkyl; lower alkoxy; halo; cyano; nitro; lower haloalkyl having 1 through 4 carbon atoms and 1 through 3 of the same or different halo atoms; lower haloalkoxy having 1 through 4 carbon atoms and 1 through 3 of the same or different halo atoms; or lower haloalkylthio having 1 through 4 carbon atoms and 1 through 3 of the same or different halo atoms;

and compatible salts thereof.

2. The compound of claim 1 wherein one of $R^1$ or $R^2$ is hydrogen.

3. The compound of claim 1 wherein one of $R^1$ or $R^2$ is methyl or ethyl and the other is hydrogen, methyl or ethyl.

4. The compound of claim 1 wherein one of $R^1$ or $R^2$ is hydrogen and the other is methyl, ethyl or propyl.

5. The compound of claim 1 wherein X is hydrogen.

6. The compound of claim 2 wherein X is hydrogen.

7. The compound of claim 3 wherein X is hydrogen.

8. The compound of claim 1 wherein R is phenyl, thienyl, furyl, naphth-1-yl, 4-fluorophenyl or substituted aryl.

9. The compound of claim 8 wherein R is phenyl, thienyl, furyl, naphth-1-yl or a monosubstituted phenyl.

10. The compound of claim 9 wherein R is phenyl, thienyl, halophenyl, or lower alkylphenyl.

11. The compound of claim 10 wherein R is phenyl, 3-thienyl, 4-fluorophenyl, 2-halophenyl, or 2-lower alkylphenyl.

12. The compound of claim 11 wherein X is hydrogen and one of $R^1$ or $R^2$ is hydrogen and the other is hydrogen, methyl or ethyl.

13. The compound of claim 1 wherein R is lower alkyl, cycloalkyl, lower alkenyl, haloalkyl or haloalkenyl.

14. The compound of claim 13 wherein one of $R^1$ or $R^2$ is hydrogen, methyl or ethyl and the other is methyl or ethyl.

15. The compound of claim 14 wherein R is methyl, ethyl or propyl.

16. The compound of claim 15 wherein one of $R^1$ or $R^2$ is hydrogen and the other is methyl or ethyl.

17. The compound of claim 16 wherein X is hydrogen.

18. A compound having the formula:

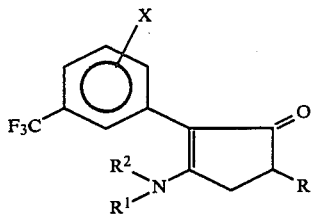

(I)

wherein R is lower alkyl, cycloalkyl having 3 through 7 carbon atoms; lower alkenyl; fluoroalkyl having 1 through 4 carbon atoms and 1 through 3 fluoro atoms, fluoro, chloro, bromo or iodo; haloalkenyl having 2 through 4 carbon atoms and 1 through 3 halo atoms independently selected from the group of fluoro, chloro, bromo, or iodo; lower alkoxyalkyl wherein the alkyl and alkoxy moieties independently have 1 through 3 carbon atoms; lower alkylthioalkyl wherein the alkyl moieties independently have 1 through 3 carbon atoms; phenyl, naphth-1-yl, inden-1-yl; 4-fluorophenyl; 4-chlorophenyl; thienyl; furyl; arylalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

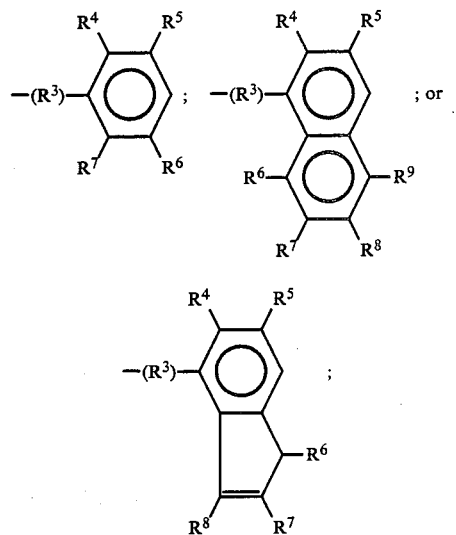

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen; and $R^3$ is a single bond or alkylene having 1 through 3 carbon atoms;

$R^1$ is hydrogen or alkyl having 1 through 4 carbon atoms;

$R^2$ is hydrogen, alkyl having 1 through 4 carbon atoms, alkenyl having 3 or 4 carbon atoms, lower alkoxycarbonylalkyl, lower alkoxyalkyl or lower alkylthioalkyl; or $R^1$ and $R^2$ together with the nitrogen atom to which they are joined form a saturated or unsaturated nitrogen heterocycle having 5 or 6 ring atoms one of which is nitrogen and the remainder are carbon atoms;

X is hydrogen, lower alkyl, lower alkoxy, halo, cyano, nitro or trifluoromethyl and can be at any available position on the phenyl ring;

and compatible salts thereof.

19. The compound of claim 18 wherein one of $R^1$ or $R^2$ is hydrogen.

20. The compound of claim 18 wherein one of $R^1$ or $R^2$ is methyl or ethyl and the other is hydrogen, methyl or ethyl.

21. The compound of claim 18 wherein one of $R^1$ or $R^2$ is methyl or ethyl and the other is hydrogen.

22. The compound of claim 19 wherein X is hydrogen and R is phenyl, thienyl, furyl, 4-fluorophenyl, 2-halophenyl or 2-lower alkylphenyl.

23. The compound of claim 22 wherein one of $R^1$ or $R^2$ is hydrogen and the other is hydrogen methyl or ethyl.

24. The compound of claim 23 wherein R is phenyl, 3-thienyl, 2-fluorophenyl 2-chlorophenyl or 2-methylphenyl.

25. The compound of claim 23 wherein R is phenyl.

26. The compound of claim 23 wherein R is phenyl and one of $R^1$ or $R^2$ is hydrogen and the other is methyl.

27. The compound of claim 23 wherein R is phenyl and one of $R^1$ or $R^2$ is hydrogen ard the other is ethyl.

28. The compound of claim 23 wherein R is 2-chlorophenyl.

29. The compound of claim 23 wherein R is 2-fluorophenyl.

30. The compound of claim 23 wherein R is 2-methylphenyl.

31. The compound of claim 23 wherein R is 3-thienyl and one of $R^1$ or $R^2$ is hydrogen and the other is hydrogen or methyl.

32. The compound of claim 18 wherein R is lower alkyl, cycloalkyl, lower alkenyl, lower fluoroalkyl or lower haloalkenyl.

33. The compound of claim 32 wherein $R^1$ and $R^2$ are independently hydrogen, methyl or ethyl.

34. The compound of claim 33 wherein R is methyl, ethyl or propyl.

35. The compound of claim 34 wherein one of $R^1$ or $R^2$ is hydrogen and the other is methyl or ethyl and X is hydrogen 36. The compound of claim 34 wherein R is ethyl and X is hydrogen.

37. The compound of claim 36 wherein one of $R^1$ or $R^2$ is methyl and the other hydrogen.

38. The compound of claim 36 wherein one of $R^1$ or $R^2$ is ethyl and the other is hydrogen.

39. The compound of claim 34 wherein R is propyl and X is hydrogen.

40. The compound of claim 39 wherein one of $R^1$ or $R^2$ is hydrogen and the other is methyl.

41. The compound of claim 39 wherein one of $R^1$ or $R^2$ is hydrogen and the other ethyl.

42. The compound of claim 32 wherein X is hydrogen.

43. The compound of claim 18 wherein X is hydrogen.

44. The compound of claim 5 wherein Y is a lower haloalkyl having 1 or 2 carbon atoms.

45. A herbicidal composition comprising a herbicidally effective amount of a compound according to claim 1, or mixtures of such compounds, and a compatible carrier.

46. A herbicidal composition comprising a herbicidally effective amount of a compound according to claim 25, or mixtures thereof, and a compatible carrier.

47. A method for preventing or destroying plants which comprises applying a herbicidally effective amount of a compound according to claim 1, or mixtures thereof, to the foliage or potential growth medium of said plants.

48. A method for preventing or destroying plants which comprises applying a herbicidally effective amount of a compound according to claim 25, or mixtures thereof, to the foliage or potential growth medium of said plants.

49. A herbicidal composition comprising a herbicidally effective amount of a compound according to claim 41 and a compatible carrier.

50. A method for controlling undesired plants which comprises applying a herbicidally effective amount of a compound according to claim 41 to the foliage or potential growth medium of said plants.

51. A plant growth regulating composition which comprises an amount of a compound according to claim 1, or mixtures thereof, effective to alter the growth pattern of plants.

52. A method for regulating the growth of plants which comprises applying to the foliage of said plants or their growth medium an amount of a compound according to claim 1, or mixtures thereof, effective to alter the growth pattern of such plants.

* * * * *